United States Patent [19]

Mettetal et al.

[11] 4,358,347

[45] Nov. 9, 1982

[54] REMOVAL OF TRACE ALDEHYDES FROM CARBOXYLIC ACIDS

[75] Inventors: Bonnie K. Mettetal, Richwood; Richard P. Kolonko, Jr., Lake Jackson, both of Tex.

[73] Assignee: The Dow Chemical Company, Midland, Mich.

[21] Appl. No.: 342,964

[22] Filed: Jan. 26, 1982

[51] Int. Cl.$^3$ .................. B01D 3/34; C07C 51/44
[52] U.S. Cl. ................................ 203/38; 203/64; 203/91; 203/DIG. 21; 562/600
[58] Field of Search ........... 203/38, 64, DIG. 21, 203/91; 562/600

[56] References Cited

U.S. PATENT DOCUMENTS 3,220,932  11/1965  Crandall ................... 203/38
3,709,928  1/1973   Murayama et al. ......... 203/38
3,725,208  4/1973   Maezawa et al. .......... 203/38
3,893,895  7/1975   Dehnert et al. ........... 203/38

Primary Examiner—Wilbur L. Bascomb, Jr.
Attorney, Agent, or Firm—A. Cooper Ancona

[57] ABSTRACT

Carbonyl impurities in acrylic acid are removed by reacting them with a 1,2-glycol prior to distillation. The acetal-type products remain as heavies in the distillation bottoms.

5 Claims, No Drawings

REMOVAL OF TRACE ALDEHYDES FROM CARBOXYLIC ACIDS

BACKGROUND OF THE INVENTION

In the manufacture of carboxylic acids frequently aldehydes are produced as by-product impurities. This is especially true in the process by which olefins are oxidized with molecular oxygen to produce unsaturated acids where aldehydes are produced as an intermediate and these frequently are found in the end product acid. Thus, acrolein is found as a minor impurity which is difficult to remove completely by distillation from acrylic acid. Neither are such by-products removed completely by the extraction process normally used as part of the purification process.

Acrolein, and other carboxylic compounds, e.g. acetaldehyde, furfural, glyoxal and crotonaldehyde, are undesirable in the unsaturated acids when these are used for making polymers and plastics because they cause (1) a prolonged induction period in the polymerization reaction, (2) color in the resulting products made from these polymers, (3) crosslinking and (4) chain termination which results in lower molecular weight polymers.

Various methods are suggested in the art for removing these aldehyde impurities from the acids. For example, U.S. Pat. No. 3,725,208 discloses a method whereby sulfuric acid, hydrazine, phenylhydrazine, aniline, monoethanolamine, ethylene diamine or glycine are added to the acid prior to its distillation. Another patent, U.S. Pat. No. 3,893,895 claims reacting the carbonyl compounds with aliphatic or aromatic amines such as hydroxylamine, a monoalkyl amine, naphthylamine to chemically bind the carbonyl compounds and then recovering said carboxylic acid by distillation.

In such processes some of the amine reacts with the acid as well as the aldehydes present with consequent loss in yield of the acid.

It has now been discovered that some of the aldehyde impurities in acrylic acid selectively react with 1,2-glycols added to the acid and, upon subsequent distillation can be removed (since the product remains in the bottoms) with no loss of acrylic acid product.

SUMMARY OF THE INVENTION

Aldehyde impurities in acrylic acid can be removed by adding a 1,2-glycol thereto prior to distillation. The aldehyde content is decreased without concurrent loss of acrylic acid yield.

DETAILED DESCRIPTION OF THE INVENTION

The addition of a 1,2-glycol to an unsaturated acid prior to its distillation will, upon heating the mixture during distillation, react with certain carbonyl impurities and allow them to remain in the bottoms of the distillation column. The acid distillate contains much less of the carbonyl impurities with no loss in yield of the desired acid.

Unsaturated acids, because of their tendency to polymerize with heat, are generally distilled under vacuum at low temperatures. The addition of the glycol in no way affects the conditions under which the purification by distillation takes place. Pressures of 20 to 30 mm Hg are employed and vapor temperatures from about 30° C. to about 40° C. are used in the purification by distillation, depending on the particular acid used. Pot temperatures no more than about 30°–40° greater than the vapor temperature are employed in the distillation. The glycol is added in at least an amount equivalent to the carbonyl content, but no more than about 1.0% based on the acid.

The process of the invention is suited for the purification of 1,2-unsaturated carboxylic acids (e.g., alkenoic acids), preferably those 1,2-unsaturated carboxylic acids having 3 to 6 carbon atoms in the chain, especially those having 3 to 4 carbon atoms such as acrylic acid and methacrylic acid. Other unsaturated acids which can be purified include ethacrylic acid, alpha hexenoic acid and the like.

The acids can be preliminarily purified by the customary measures such as extraction and distillation before use of the process of the invention, especially to reduce the content of carbonyl compounds, i.e., aldehydes and ketones below about 5%, preferably to below about 2%. The process of the invention is especially suited to the purification of all unsaturated carboxylic acids produced by vapor phase oxidation of an alkene or alkenal and which are largely freed of by-products by known processes. This type of recovered unsaturated carboxylic acid generally contains less than 2%, for the most part less than 1% of carbonyl compounds. The carbonyl compounds, for example, in the case of acrylic acid are acrolein, formaldehyde, acetaldehyde, glyoxal and furfural. Other carbonyl compounds which can be removed include, for example, methacrolein, crotonaldehyde, hexen-2-al, and acetone.

The reaction of the glycol with the carbonyl impurities is believed to form cyclic acetals of the formula

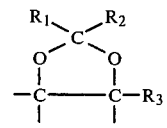

wherein $R_1$, $R_2$ and $R_3$ are lower alkyl groups, having from 1 to 3 carbon atoms; $R_1$ and $R_3$ can be hydrogen; and $R_2$ can be alkenyl.

These acetals are heavier compounds having higher boiling points than the acid and thus remain in the bottoms of the distillation process.

The following examples are representative of the process of the invention:

EXAMPLE 1

Into a one liter glass distillation pot fitted with a distillation column, having ~10 plates and cooled with ice water, was placed 1060.4 g. of crude acrylic acid from a propylene oxidation process and to this 10.76 g. (1.01% by wt.) of ethylene glycol was added. The carbonyl content (C=O) was 0.98% by weight in the undistilled acid. After distillation in the presence of the glycol under a pressure of 20 mm Hg and at a vapor temperature of 33° C. the C=O content of the distillate was 0.038% by weight, a decrease of 96% in carbonyl content.

We claim:

1. In a process for removing carbonyl impurities from an unsaturated acid by adding a compound to said acid which will react with said impurities, the improvement of employing a 1,2-glycol as said added compound, reacting by heating and subsequently distilling the unsaturated acid to obtain an acid having a lower content of carbonyl impurities.

2. The process of claim 1 wherein the unsaturated acid is acrylic acid.

3. The process of claims 1 or 2 wherein the 1,2-glycol is ethylene glycol.

4. The process of claim 3 wherein the distillation is conducted under reduced pressure.

5. The process of claim 4 wherein the pressure is from about 20 to about 30 mm Hg.

* * * * *